(12) United States Patent
Holman et al.

(10) Patent No.: US 8,845,581 B2
(45) Date of Patent: Sep. 30, 2014

(54) MEDICAL BALLOON DEFLATION

(75) Inventors: Thomas J. Holman, Princeton, MN (US); Afsar Ali, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1005 days.

(21) Appl. No.: 11/599,049

(22) Filed: Nov. 14, 2006

(65) Prior Publication Data
US 2008/0114294 A1 May 15, 2008

(51) Int. Cl.
A61M 29/02 (2006.01)
A61M 31/00 (2006.01)
A61M 25/10 (2013.01)

(52) U.S. Cl.
CPC ....... *A61M 25/1038* (2013.01); *A61M 25/1002* (2013.01)
USPC .............. 604/96.01; 604/103; 604/103.06; 604/103.14

(58) Field of Classification Search
USPC .............. 604/96.01, 103, 103.06, 103.14
See application file for complete search history.

(56) References Cited

U.S. PATENT DOCUMENTS

| | | | |
|---|---|---|---|
| 4,941,877 A | 7/1990 | Montano, Jr. | |
| 5,352,199 A * | 10/1994 | Tower | 604/103.07 |
| 5,501,759 A * | 3/1996 | Forman | 156/272.8 |
| 5,545,132 A | 8/1996 | Fagan et al. | |
| 5,759,172 A | 6/1998 | Weber et al. | |
| 5,826,588 A | 10/1998 | Forman | |
| 5,853,389 A | 12/1998 | Hijlkema | |
| 6,010,480 A * | 1/2000 | Abele et al. | 604/103.06 |
| 6,030,369 A * | 2/2000 | Engelson et al. | 604/264 |
| 6,030,405 A * | 2/2000 | Zarbatany et al. | 606/191 |
| 6,193,738 B1 * | 2/2001 | Tomaschko et al. | 606/194 |
| 6,242,063 B1 * | 6/2001 | Ferrera et al. | 428/35.2 |
| 6,428,568 B2 * | 8/2002 | Gaudoin et al. | 623/1.11 |
| 6,544,224 B1 * | 4/2003 | Steese-Bradley | 604/103.06 |
| 6,585,926 B1 | 7/2003 | Mirzaee | |
| 6,702,802 B1 * | 3/2004 | Hancock et al. | 604/524 |
| 6,989,025 B2 | 1/2006 | Burgmeier et al. | |
| 7,004,963 B2 * | 2/2006 | Wang et al. | 623/1.11 |
| 7,056,276 B2 * | 6/2006 | Nakano et al. | 600/3 |
| 7,485,250 B2 * | 2/2009 | Boatman et al. | 264/494 |
| 7,963,942 B2 * | 6/2011 | Chen | 604/103.14 |
| 2003/0144683 A1 | 7/2003 | Sirhan et al. | |
| 2003/0163148 A1 | 8/2003 | Wang et al. | |
| 2004/0225318 A1 | 11/2004 | Eidenschink et al. | |
| 2005/0015046 A1 | 1/2005 | Weber et al. | |
| 2005/0027344 A1 | 2/2005 | Eidenschink | |

(Continued)

FOREIGN PATENT DOCUMENTS

| | | |
|---|---|---|
| EP | 0 783 897 A2 | 7/1997 |
| EP | 1 120 129 A1 | 8/2001 |
| WO | WO 2006/065356 A1 | 6/2006 |
| WO | 2006/089115 | 8/2006 |

OTHER PUBLICATIONS

Jan Weber et al., "Medical Balloons and Methods of Making the Same", U.S. Appl. No. 11/355,392, filed Feb. 16, 2006, 48 pp.

(Continued)

*Primary Examiner* — Quynh-Nhu H Vu
(74) *Attorney, Agent, or Firm* — Vidas, Arrett & Steinkraus, P.A.

(57) ABSTRACT

Medical balloons are energetically treated to form regions that facilitate deflation to a desirable configuration.

18 Claims, 7 Drawing Sheets

(56) References Cited

U.S. PATENT DOCUMENTS

| | | |
|---|---|---|
| 2005/0146085 A1 | 7/2005 | Holman et al. |
| 2005/0177130 A1 | 8/2005 | Konstantino et al. |
| 2005/0228429 A1* | 10/2005 | Burgmeier et al. ........... 606/194 |
| 2006/0167407 A1 | 7/2006 | Weber et al. |
| 2006/0182873 A1 | 8/2006 | Klisch et al. |
| 2007/0244501 A1* | 10/2007 | Horn et al. ................... 606/194 |

OTHER PUBLICATIONS

Thomas Bahners et al., "Photon-based processes for surface modification of synthetic fibers", 2004, Polymer Surface Modification: Relevance to Adhesion, vol. 3, pp. 97-106.

Communication Relating to the Results of the Partial International Search Report, International Application Serial No. PCT/US2007/078671, Jun. 3, 2008, 2 pp.

* cited by examiner

MEDICAL BALLOON DEFLATION

TECHNICAL FIELD

This invention relates to medical balloon deflation.

BACKGROUND

The body includes various passageways such as arteries, other blood vessels, and other body lumens. These passageways sometimes become occluded, e.g., by a tumor or restricted by plaque. To widen an occluded body vessel, balloon catheters can be used, e.g., in angioplasty.

A balloon catheter can include an inflatable and deflatable balloon carried by a long and narrow catheter body. The balloon is initially folded around the catheter body to reduce the radial profile of the balloon catheter for easy insertion into the body.

During use, the folded balloon can be delivered to a target location in the vessel, e.g., a portion occluded by plaque, by threading the balloon catheter over a guide wire emplaced in the vessel. The balloon is then inflated, e.g., by introducing a fluid into the interior of the balloon. Inflating the balloon can radially expand the vessel so that the vessel can permit an increased rate of blood flow. After use, the balloon is deflated and withdrawn from the body. It is desirable that upon deflation, the balloon forms a predictable low profile configuration that facilitates withdrawal from the body.

SUMMARY

In an aspect, a method of making an inflatable medical balloon is described. The method includes providing a generally cylindrical inflatable balloon wall or balloon parison formed of polymer, forming a series of first ablated regions wherein the polymer is removed to enhance flexibility of the wall, forming a series of second treated regions alternating with the first ablated regions, the second treated regions being formed by UV radiation exposure, heating, or ion implantation, such that the second treated regions have less flexibility than the first ablated regions.

In another aspect, a method of making an inflatable medical balloon is described. The method includes providing a generally cylindrical inflatable balloon wall or balloon parison formed of polymer and forming a series of first treated regions where the polymer crystallinity is increased, but no polymer is removed from the balloon in the first treated regions, wherein upon deflation the balloon folds according to the locations of the series of first treated regions.

In another aspect, an inflatable medical balloon device is described. The device includes a generally cylindrical balloon wall formed of polymer. The wall includes a series of first ablated regions where polymer has been removed to enhance flexibility and a series of second treated regions alternating with the ablated regions, and third regions. The second treated regions having a flexibility less than the ablated regions but more flexibility than the third regions of the balloon.

In an aspect, a medical device including an inflatable balloon having a generally cylindrical wall formed of polymer is described. The wall includes a series of first treated regions where the crystallinity of the polymer is greater compared to the crystallinity of the polymer in a series of second regions formed of the polymer, the first treated regions having a flexibility different than the second regions, wherein the balloon device upon deflation folds according to the locations of the first treated locations.

In an aspect, a medical device including an inflatable balloon having a generally cylindrical wall formed of polymer is described. The wall includes a series of ablated groove regions. The groove regions have grooves with a depth of between about 1-2% of a thickness of the wall and the grooves regions have at least about 4% greater polymer crystallinity than polymer regions outside the grooved regions.

In an aspect, the invention features a method including providing a medical device as described herein, arranging the balloon into lobes and wrapping the lobes, delivering the balloon into the body, inflating the balloon, and deflating the balloon, whereby the balloon forms at least three lobes.

In an aspect, a medical device including an inflatable balloon having a generally cylindrical wall formed of polymer is described. The wall has a series of ablated groove regions, the groove regions having grooves with a depth of between about 1-2% of a thickness of the wall and the grooves regions having at least about 4% greater polymer crystallinity than polymer regions outside the grooved regions.

In an aspect, a medical device including an inflatable balloon having a generally cylindrical wall formed of polymer is described. The wall has a series of regions having at least about 4% greater polymer crystallinity than polymer areas outside the regions, wherein the surface of the balloon in the regions has raised nodules of polymer that cause the polymer areas outside the regions to have a greater effective thickness than the regions.

Embodiments may include one or more of the following advantages. A balloon can be formed that folds after inflation into a desired configuration which has a low profile that facilitates withdrawal from the vessel after angioplasty and/or stent delivery. Balloons treated using two or more different processes can enhance the precision and reliability of balloon folding. The processes can be used to define regions of different flexibility in a desired pattern to induce a desired fold profile. The different processes can employ different techniques such as laser ablation, hot stick, $CO_2$ laser, and ion beam treatment which can induce different effects to the balloon material, such as material removal, cross-linking, and carbonization.

Still further aspects, features and advantages follow.

DESCRIPTION OF DRAWINGS

Like reference symbols in the various drawings indicate like elements.

DETAILED DESCRIPTION

Figure 1A:
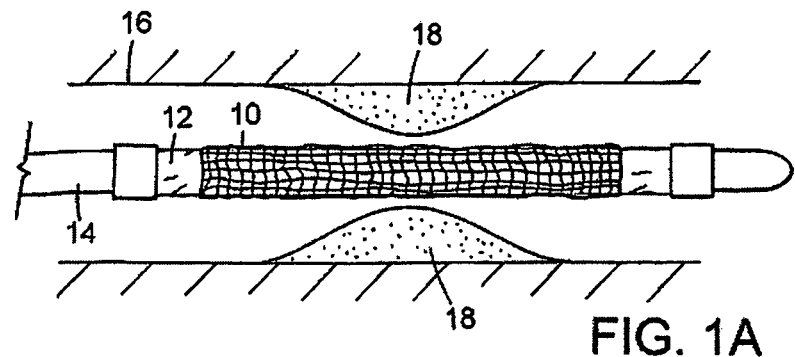
FIGS. 1A-1C are partial cross-sectional views illustrating delivery of a stent in a collapsed state over a balloon, expansion of the stent by inflation of the balloon, and deflation and withdrawal of the balloon.
Figure 1B:
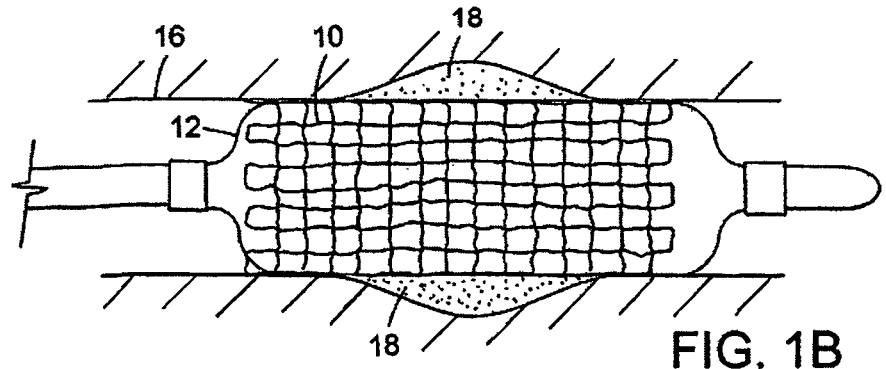
Figure 1C:
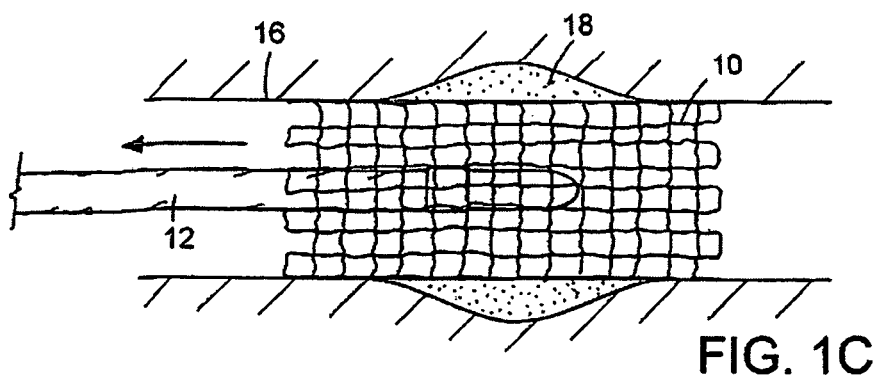

Referring to FIGS. 1A-1C, stent 10 is placed over a balloon 12 carried near a distal end of a catheter 14, and is directed through a lumen 16, e.g., a blood vessel such as the coronary artery, until the portion carrying the balloon and stent reaches the region of an occlusion 18 (FIG. 1A). The stent 10 is then radially expanded by inflating the balloon 12, and is pressed against the vessel wall with the result that occlusion 18 is compressed, and the vessel wall surrounding it undergoes a radial expansion (FIG. 1B). The pressure is then released from the balloon and the catheter is withdrawn from the vessel (FIG. 1C).

Figure 2A:
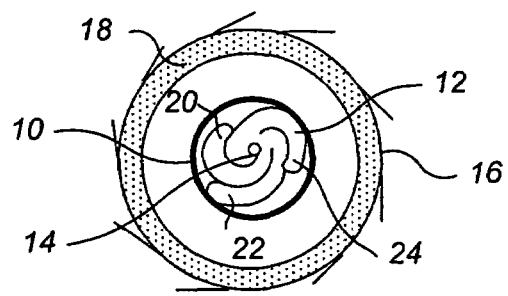
FIGS. 2A-2C are end on cross-sectional views of a balloon in conditions corresponding to FIGS. 1A-1C.
Figure 2B:
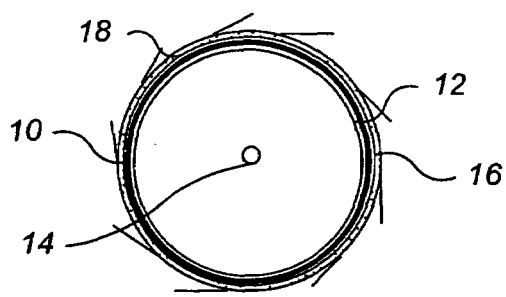
Figure 2C:
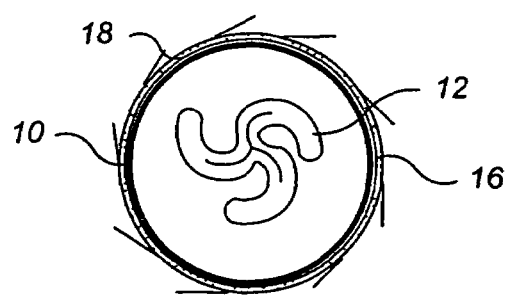

Referring as well to FIGS. 2A-2C, during delivery to the treatment site, the balloon is in a folded condition in which the balloon material is arranged into three flaps or lobes 20, 22, 24 and the lobes are wrapped around the catheter body to provide a low profile (FIG. 2A). During inflation, inflation fluid is introduced into the balloon and the lobes unwrap such that at full inflation the balloon forms a substantially circular cross section of a diameter sufficient to carry out the desired treatment, such as an angioplasty and/or stent delivery procedure (FIG. 2B). After full expansion, the inflation fluid is withdrawn from the balloon and the balloon forms three lobes (FIG. 2C). Forming two or more lobes, such as three, four, five, six, seven or more lobes, on deflation reduces the profile of the balloon which facilitates withdrawal of the balloon by, for example reducing the likelihood of snagging the stent and minimizing friction or abrasion with the body lumen.

Figure 3A:
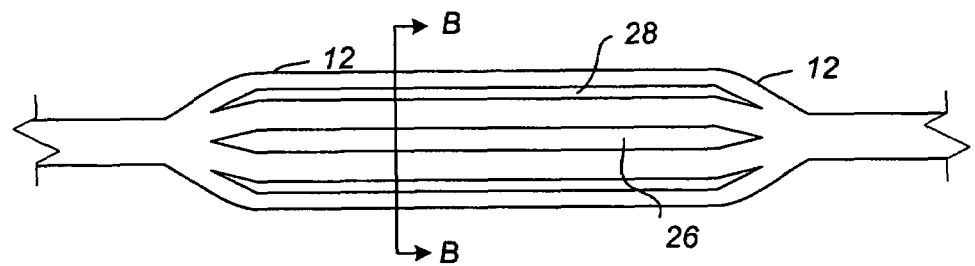
FIG. 3A is a side view of a balloon in an inflated state.
Figure 3B:
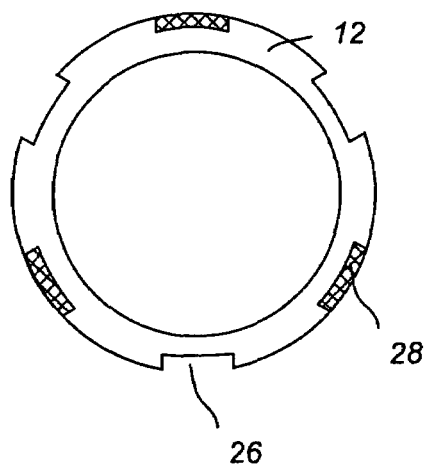
FIG. 3B is a cross-sectional view through the wall of the balloon in FIG. 3A.
Figure 3C:
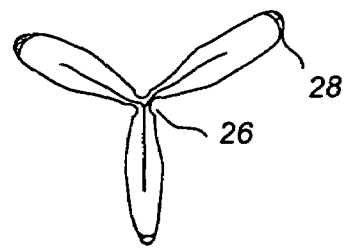
FIG. 3C is a cross-sectional view similar to FIG. 3B with the balloon in a refolded deflated state.

Referring as well to FIGS. 3A-3C, the formation of a desired lobe configuration is facilitated by treating the balloon wall to modify its chemical and/or mechanical properties, such as its stiffness or flexural strength, in different ways in different regions. Referring particularly to FIGS. 3A and 3B, the balloon 12 has two series of modified regions 26, 28 which alternate with one another and with regions of unmodified balloon material. The regions 26, 28 have been treated by different processes so that their properties differ from each other. Referring as well to FIG. 3C, in the embodiment illustrated, the regions 26 have been modified so that, upon balloon deflation, they form the valleys between lobes and the regions 28 form the apexes of the lobes.

Figure 4A:
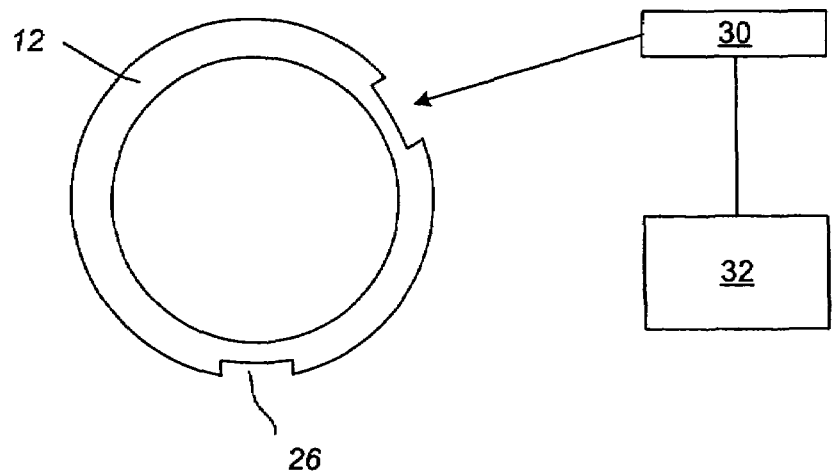
FIG. 4A is a schematic of the balloon during a first treatment process.
Figure 4B:
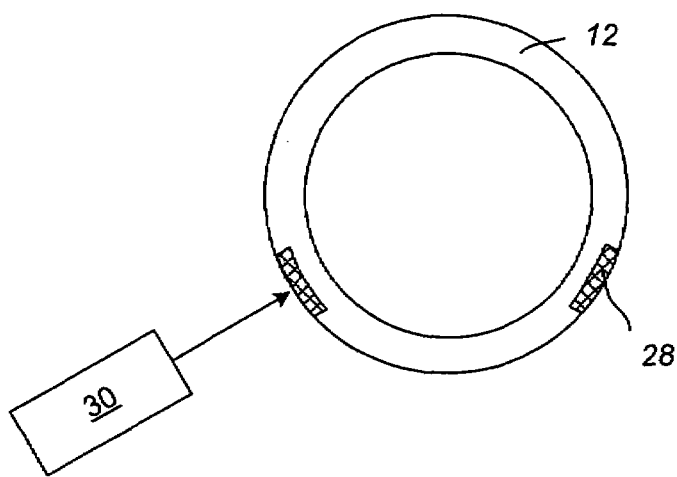
FIG. 4B is a schematic of the balloon in FIG. 4A undergoing a second treatment process.

Referring to FIGS. 4A and 4B, the regions 26, 28 are formed by separate processes of ablating and modifying crystallinity of the balloon material. To both ablate and increase the crystallinity of the material, regions 26, 28 of the balloon are exposed to ultraviolet radiation. Referring to FIG. 4A, the regions 26 are exposed to an ultraviolet radiation from a laser 30 controlled by a controller 32 to deliver energy to the exposed regions such that the laser fluence exceeds the ablation threshold of the material. Chemical bonds are broken and the material is fractured into energetic fragments which leave the ablation zone. It is theorized that most of the energy is deposited in the ejected material so there is little thermal damage to surrounding materials. The high energy input to regions 26 removes some of the thickness of the material and therefore reduces the stiffness of these regions more than regions exposed to lower total energy or the unmodified polymer. As a result, the more flexible regions 26 tend to fold and collapse more quickly as the balloon is deflated, forming valleys. Referring to FIG. 4B, the regions 28 are formed by exposure of ultraviolet radiation at a lower fluence, that is below the ablation threshold. The regions 28 that are treated with the lower energy have increased crystallinity, which increases the stiffness or modulus of these regions. The increased stiffness causes the treated regions to be less flexible than the unmodified regions and thus the balloon is less likely to bend in the stiffer regions than in the unmodified regions. The stiffer regions 28 form the apexes of the lobes upon refolding. The balloon thus has three regions, where each of the three regions has a different flexibility due to different amount of material thickness or crystallinity in each region.

Exposure to UV radiation can increase the crystallinity of the polymer and/or ablate or remove polymeric material. If the balloon is ablated, the amount of material removed can be for example, about 0.1-15%, such as 0.5 to 2.5% of the balloon wall thickness. If the balloon's crystallinity is modified without substantial ablation effects, the crystallinity of the polymer can be increased by about 2 to 90%, e.g., 2-5%, 5-10%, 10-20%, 20-40%, 40-60%, 60-70%, 70-80%, 80-90% or 20-80%, compared to the unmodified polymer. In some embodiments, the crystallinity percentage can be two, three or four times after modification than prior to modification. The amount of crystallinity and/or material removal can be selected to finely tailor the balloon refolding properties. Whether material is removed or not is dependent on the fluence of the laser and the material from which the balloon is formed. The amount of change in crystallinity can be controlled by controlling the energy delivered to the exposed regions, such as by controlling the time of exposure, the fluence and/or the wavelength of radiation. Crystallinity can be increased by increasing the exposure time at a low fluence. A suitable laser is a multigas UV excimer laser at a wavelength of about 193 nm. Ultraviolet ablation is further described in U.S. Pat. No. 4,911,711. Suitable ablation and control systems are available from Coherent Lambda Physiks, in Goettingen, Germany. Crystallinity can be measured by WAX/SAX x-ray diffraction. Crystallinity measurements can be made at various vendors, such as the University of Minnesota Shepard characterization lab.

Figure 5A:
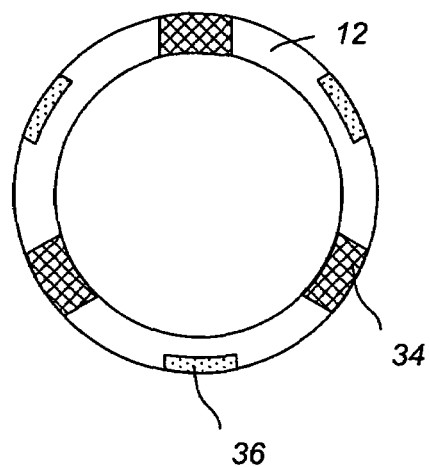
FIG. 5A is a schematic of the balloon treated with first and second treatment processes.
Figure 5B:
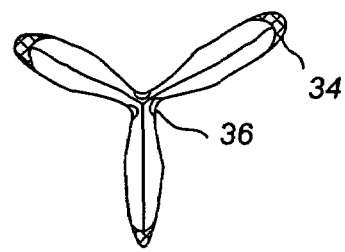
FIG. 5B is a schematic of the balloon a folded state.

Referring as well to FIGS. 5A and 5B, in other embodiments regions 34, 36 can be formed by using different modification techniques. The regions 34, 36 are each regions with increased crystallinity, but one region 34 has greater crystallinity than the other region 36. The region 34 with the greatest crystallinity forms the apex of the fold when the balloon is collapsed. The region 36 with somewhat increased crystallinity, that is the region where the crystallinity is greater than the unmodified balloon material but less than the region 34 with the greatest crystallinity, tends to fold into the valleys between the lobes of the collapsed balloon.

As an alternative to treating the balloon with two different treatment methods, a balloon can be treated with only one treatment method that increases crystallinity without substantially removing material from the surface of the balloon, that is, without ablation. The thickness of the balloon in the treated and untreated regions can be substantially the same. Crystallinity can be increased by heating the polymer material to between the glass transition temperature and the melt flow temperature. Within this temperature range, crystals begin to form or crystals that were previously present grow larger. Crystallinity can be changed only on the surface or can be changed throughout the depth of the balloon wall.

Suitable techniques for inputting heat into the balloon, such as UV lasers, affect primarily the surface of the balloon. For example, a UV laser may penetrate only part way into a polymer surface, such as 1-60 Angstroms into the balloon. Other heating techniques can penetrate more deeply into the material. With some methods of applying energy, the energy not only penetrates into the material, but radiates isotropically. This heating is considered to be massive or bulk heating of the material, because more than just the surface of the material is heated. A laser, such as a $CO_2$ laser, an IR laser, a YAG laser, a diode laser or any another suitable photon source, a heat stick, i.e., a conductive material connected to a heat cartridge, or an RF generator can be used to apply heat to the balloon. In the case of an RF generator, a jelly having metal particles can be applied to the regions to be treated. If a laser is used to apply heat to the balloon, the balloon can be filled with a fluid to absorb the heat and prevent other portions of the balloon from being simultaneously treated. As noted herein, the amount of crystallinity can be controlled, such as by controlling the amount of time that energy is input into the balloon or controlling the energy output by the energy input device. To focus the heat on particular regions of the balloon, a mask can be used or the device for applying the heat can be focused only in the region where crystallization is desired. With some methods of treating the balloon, the depth of the crystallization can determine whether the treated region ends up on the apex or the valley of a fold. Surface treatment with a UV laser tends to form treated regions that are in the valleys of the folds of the balloon, where treatment with a $CO_2$ laser or hot stick forms treated regions that are on the apex of the folds a balloon.

Flexibility or stiffness variations can also be formed by other techniques, such as ion beam exposure and mechanically by cutting regions of the balloon wall. All of these techniques can be used in any combination to provide desired properties to the balloon. Ion beam treatment is further described in U.S. application Ser. No. 11/533,588, filed Sep. 20, 2006, and U.S. application Ser. No. 11/355,392, filed Feb. 16, 2006. The treated regions can be formed by application of energy on the balloon directly or on a polymer tubular parison that is subsequently formed or blown into a balloon, e.g. by free inflation or blow molding. Balloon formation is described further in U.S. Pat. No. 4,963,313.

Polymers suitable for forming the balloon include biaxially oriented polymers, thermoplastic elastomers, engineering thermoplastic elastomers, polyethylenes, polyethylene terephthalate (PET), polybutylenes, polyamides (e.g. nylon 66), polyether block amides (e.g., PEBAX®), polypropylene (PP), polystyrene (PS), polyvinyl chlorides (PVC), polytetrafluorethylene (PTFE), polymethylmethacrylate (PMMA), polyimide, polycarbonate (PC), polyisoprene rubber (PI), nitrile rubbers, silicone rubbers, ethylene-propylene diene rubbers (EPDM), butyl rubbers (BR), thermoplastic polyurethanes (PU) (e.g., those based on a glycol ether and an isocyanate, such as PELLETHANE®). In particular embodiments, a poly(ether-amide) block copolymer having the general formula

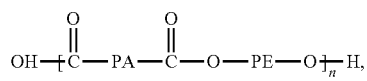

in which PA represents a polyamide segment, e.g., nylon 12, and PE represents a polyether segment, e.g., poly(tetramethylene glycol) is utilized. Such polymers are commercially available from ARKEMA under the tradename PEBAX®. The balloon can be formed of single polymer or of multiple polymers, e.g. by coextrusion.

As noted above, the fluence threshold depends on the balloon material and on the type of wavelength of energy input into the material. Suitable UV lasers for treating the balloon have a wavelength between about 150-450 nm, such as 157, 193, 248, 308 or 351 nm. For treating a PET or a PEBAX® balloon with a 193 nm laser, less than about 150 mJ/cm$^2$, such as between about 60-70 mJ/cm$^2$ will avoid ablating the balloon material. Other combinations of materials and lasers will have different thresholds of fluence to avoid ablation.

In addition to the linear treated regions described, the treated regions can be arranged in other configurations to enhance refolding. In some embodiments, the treated regions spiral around the balloon. In some embodiments the treated regions are only on the cones, only on the body or both on the body and the cones of the balloon. In yet other embodiments the treated regions are not formed in a contiguous line, but are formed as a series of dots, dashes or shapes which together determine where the balloon will fold upon deflation.

Balloons can be treated to facilitate formation of two or more, preferably three or four or more lobes. The lobes that form when the balloon is deflated after use in a lumen can form at locations corresponding to the locations of the lobes formed and wrapped for delivery or the lobes can form at different locations on deflation. When the balloon is able to collapse into a multilobed profile, the diameter of the collapsed balloon is less than when the balloon flattens or pancakes. This smaller profile can facilitate in removing the collapsed balloon from a lumen, such as a stent or vessel. That is, the folded balloon can be smoothly removed from the lumen with less risk of sticking or catching on the lumen on removal. Any number of treated regions can be formed on the surface of the balloon, such as four, five, six, seven or eight treated regions. The balloons can be used in vascular and nonvascular applications, including coronary, peripheral, carotid, esophageal or uretheral applications.

EXAMPLE

A 3.0×16 mm TAXUS® Liberté™ OTW (PEBAX® 7233) polymer balloon available from Boston Scientific, Natick, Mass., is inflated to a pressure of 2 psi and exposed to UV radiation using a Lambda 210i, multigas UV excimer laser (available from Coherent Lambda Physiks, in Goettingen, Germany) operating at a pulse duration of 29 ns and at a wavelength of 193 nm with an attenuator set at 30 VA to deliver a fluence of 30 mJ/cm$^2$, which is below the ablation threshold of PEBAX®, which is around 60-70 mJ/cm$^2$. The beam from the laser is about 1 mm wide and about 5 mm long. Three linear regions approximately 1 mm in width spaced equidistantly about the balloon are exposed. The regions are exposed at a shot spacing of 400 microns. The exposed regions became opaque and have a crystallinity of about 22%, where the untreated regions has a crystallinity of about 16%.

Figure 6:
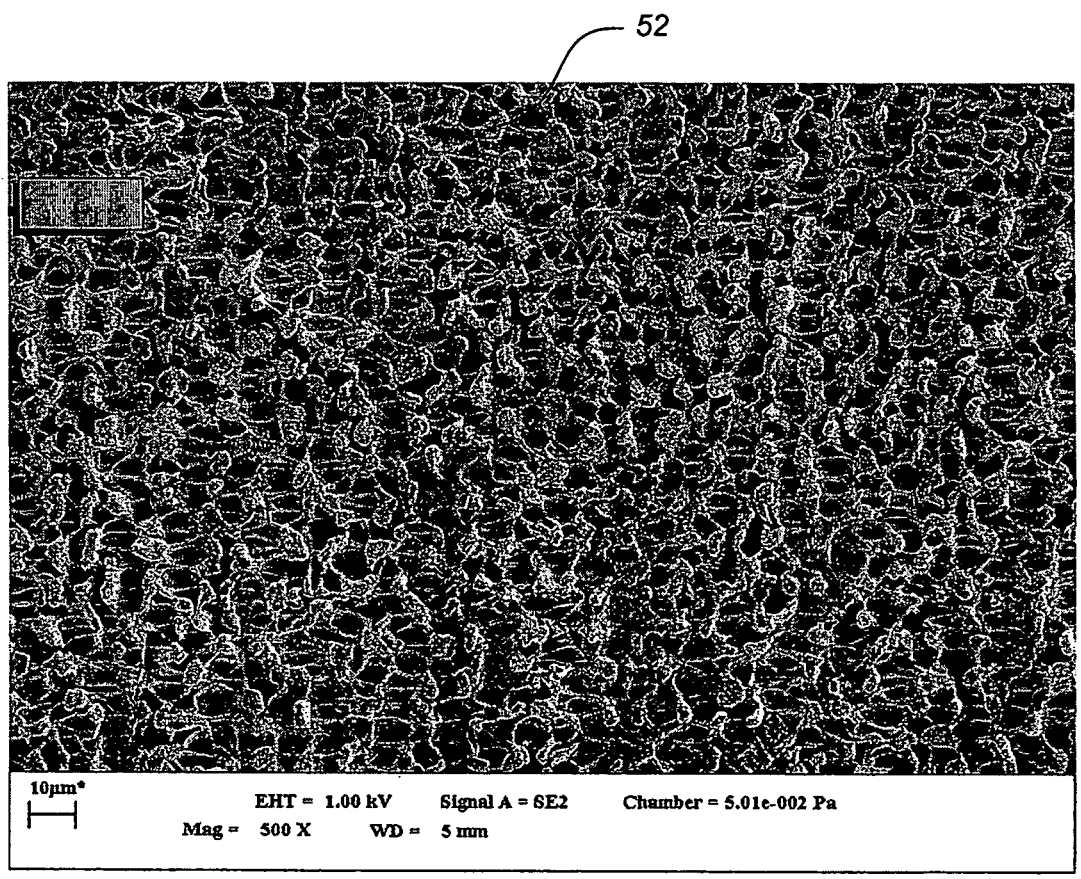
FIG. 6 is a scanning electron microscope image of a modified surface.

Referring to FIG. 6, an effect of some heat applications, such as application of UV laser, is to rearrange material at the surface of the balloon. A magnified view of a balloon surface that is crystallized using a UV laser shows nodules 52. The balloon is a TAXUS® Liberté™ OTW (PEBAX® 7233) polymer balloon available from Boston Scientific, Natick, Mass., and is exposed to UV radiation using a Lambda 210i, multigas UV excimer laser (available from Coherent Lambda Physiks, in Goettingen, Germany) operating at a wavelength of 193 nm with an attenuator set at 30 VA to achieve an output of 30 mJ/cm$^2$. Forming the nodules 52 does not remove polymer material from the balloon wall, but rearranges the material on the balloon surface and can reduce the effective wall thickness between the nodules. A non-treated balloon wall would appear smooth and free of nodules. Nodules 52 are observed when the balloon is treated with a UV laser, but are not observed with other treatments, such as $CO_2$ laser or hot stick. The UV laser treated regions also appear to be opaque, due to the surface modification.

Figure 7A:
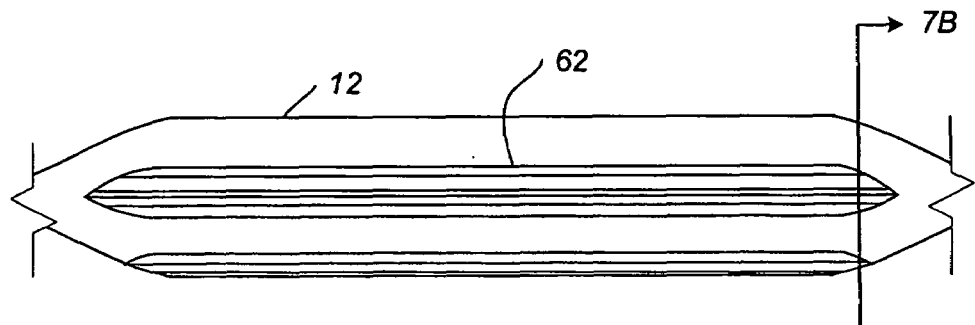
FIG. 7A is a schematic side view of an inflated balloon with one type of treated region.
Figure 7B:
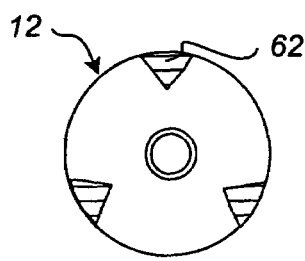
FIG. 7B is a schematic end view of an inflated balloon with one type of treated region.
Figure 8A:
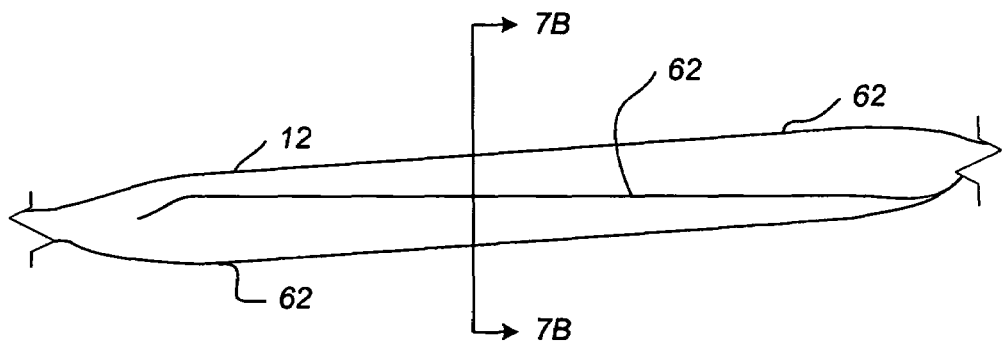
FIG. 8A is a schematic side view of an inflated balloon with one type of treated region.
Figure 8B:
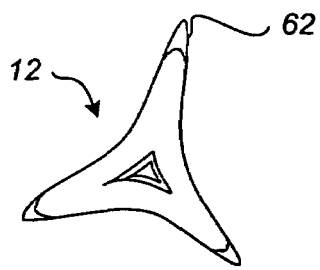
FIG. 8B is a schematic end view of an inflated balloon with one type of treated region.

Referring to FIG. 7A, a treated balloon has three stripes 62 made using UV laser. All stripes extend past the balloon body-cone transition area on both the distal and proximal ends. Each stripe has 1 mm width. Referring to FIG. 7B, the end view shows the three treated regions on the cone of the balloon. Referring to FIGS. 8A and 8B, the folded balloon forms three lobes. The profile of the tri-folded balloon is about 30% less than when compared to a pancaked balloon, or a balloon that has not been treated and flattens rather than folds when deflated. When a 3.0×16 mm TAXUS® Liberté™ OTW balloon is treated in regions to enhance refolding, the refolding profile was found to be 2.85 mm. A similar balloon that is not treated pancakes to have a profile of 4.16 mm.

All patents, patent applications, and publications referenced herein are incorporated by reference in their entirety.

Still further embodiments are in the following claims.

What is claimed is:

1. An inflatable medical balloon device, comprising:
  a generally cylindrical balloon wall formed of polymer, wherein the wall includes a series of first ablated regions, a series of second treated regions alternating circumferentially about the balloon with the first ablated regions, and third unmodified regions alternating circumferentially about the balloon between the first ablated regions and the second treated regions,
    wherein the second treated regions have a flexibility less than the first ablated regions, and the second treated regions are regions of increased crystallinity compared to the third unmodified regions.

2. The inflatable medical balloon device of claim 1, wherein when the balloon is deflated, the first ablated regions form valleys and the second treated regions form lobes.

3. The inflatable medical balloon device of claim 2, wherein the second treated regions form apexes of the lobes.

4. The inflatable medical balloon device of claim 1, wherein the balloon has a constant inner diameter in an inflated state.

5. An inflatable medical balloon device, comprising:
  a generally cylindrical balloon wall formed of polymer wherein the wall includes a series of first treated regions where the crystallinity of the polymer is greater compared to the crystallinity of the polymer in a series of second regions formed of the polymer, the first treated regions having a flexibility different than the second regions, wherein the balloon device upon deflation folds according to the locations of the first treated locations,
    wherein the first treated regions alternate circumferentially with the second regions.

6. The balloon device of claim 5, wherein the first treated regions and the second regions have substantially the same thickness.

7. The balloon device of claim 5, wherein the balloon forms lobes on deflation according to the locations of the first treated regions.

8. The balloon device of claim 7, wherein the first treated regions are at the valleys between the lobes.

9. The balloon device of claim 7, wherein the balloon forms three or more lobes on deflation.

10. The balloon device of claim 5, including a stent positioned over the balloon.

11. The balloon device of claim 5, wherein the first treated regions have a crystallinity that is at least twice the crystallinity of the second regions.

12. The balloon device of claim 5, wherein the first treated regions have a surface with polymer nodules.

13. The balloon device of claim 5, further comprising third treated regions alternating with the first treated regions, the third treated regions and the first treated regions having a different flexibility than the second regions of the balloon.

14. The balloon device of claim 13, wherein the third treated regions are at the apex of lobes formed upon deflation.

15. The balloon device of claim 13, wherein the third treated regions are ablated regions having a thickness less than the thickness of the balloon wall in the second regions.

16. A medical device, comprising:
  an inflatable balloon having a generally tubular wall formed of polymer, the wall including a series of ablated groove regions, the ablated groove regions having grooves with a depth of between about 1-2% of a thickness of the wall and at least about 4% greater polymer crystallinity than second regions outside the ablated groove regions,
    wherein the ablated groove regions alternate radially with the second regions.

17. The medical device of claim 16, comprising third treated regions having flexibility less than the ablated groove regions.

18. The medical device of claim 16, wherein the balloon forms three or more lobes on deflation.

* * * * *